United States Patent [19]

Sauer et al.

[11] Patent Number: 5,977,011

[45] Date of Patent: *Nov. 2, 1999

[54] CATALYST, PROCESS FOR ITS PREPARATION, AND USE FOR SYNTHESIS OF METHYL MERCAPTAN

[75] Inventors: Joerg Sauer, Rodenbach; Lukas von Hippel, Alzenau; Dietrich Arntz, Oberursel; Wolfgang Boeck, Langenselbold, all of Germany

[73] Assignee: Degussa Huls, Frankfurt am Main, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/885,042

[22] Filed: Jun. 30, 1997

[30] Foreign Application Priority Data

Sep. 26, 1996 [DE] Germany ............................ 196 39 520

[51] Int. Cl.$^6$ ............................ B01J 23/24; C07C 319/08
[52] U.S. Cl. ............................ 502/305; 502/415; 568/60; 568/70
[58] Field of Search ........................ 568/60, 70; 502/415, 502/305

[56] References Cited

U.S. PATENT DOCUMENTS 2,820,062  1/1958  Folkins et al. .......................... 260/609

OTHER PUBLICATIONS

Datenbank Caplus: Chemical Abstracts, vol. 120, Abstract 120: 190890, Maschkin, V.Yu. in App. Catalyst, A (1994) 109(1), 45–61.

A.V. Mashkina et al.: Activity of Tungstate Catalysts in the Synthesis of Methyl–mercaotane from Methanol and Hydrogen Sulfide, React. Kinet. Catal. Letter vol. 36, No. 1, 159–164 1988).

Primary Examiner—Gary Geist
Assistant Examiner—Jean F Vollano
Attorney, Agent, or Firm—Smith, Gambrell & Russell

[57] ABSTRACT

A catalyst for the synthesis of methyl mercaptan from hydrogen sulfide and methanol as well as a process for preparation of the catalyst. The catalyst is an active aluminum oxide onto which 5 to 25% by weight potassium tungstate is deposited as an activator. A two-stage impregnation with intermediate drying produces a catalyst which exhibits distinctly better selectivity for formation of methyl mercaptan than catalysts obtained by single-stage impregnation.

20 Claims, 3 Drawing Sheets

5,977,011

CATALYST, PROCESS FOR ITS PREPARATION, AND USE FOR SYNTHESIS OF METHYL MERCAPTAN

INTRODUCTION AND BACKGROUND

The present invention relates to a catalyst for the synthesis of methyl mercaptan from methanol and hydrogen sulfide, and a process for preparing this catalyst. In a further aspect, the present invention relates to a process for the synthesis of methyl mercaptan utilizing the aforesaid catalyst.

Methyl mercaptan is an important industrial intermediate for the synthesis of methionine and for production of dimethyl sulfoxide and dimethyl sulfone. At present it is produced predominantly from methanol and hydrogen sulfide by reaction in the presence of an aluminum oxide catalyst. Methyl mercaptan is usually synthesized in the gas phase at temperatures from 300° C. to 500° C. and at pressures of 1 to 25 bar.

The reaction gas mixture contains not only the methyl mercaptan produced but also the unreacted starting materials and byproducts such as dimethyl sulfide and dimethyl ether, as well as gases which are inert in this reaction, such as methane, carbon monoxide, hydrogen and nitrogen. The methyl mercaptan produced is separated from this reaction mixture.

If the reaction of hydrogen sulfide and methanol is carried out in the presence of the catalyst at elevated pressure so that the product of methyl mercaptan preparation is at elevated pressure (more than 7 bar), methyl mercaptan can, for example, be separated by washing with methanol at a washer head temperature of 25° C., as described in German patent 17 68 826. If the reaction product is at normal pressure, it is necessary to recover the product at temperatures down to −60° C. (Japanese Laid-Open Patent Application 45-10728) to obtain the methyl mercaptan in liquid form. The unreacted hydrogen sulfide can be returned to the reactor, as described in German Patent 17 68 826.

The highest possible selectivity is required in the catalytic reaction of methanol and hydrogen sulfide to produce methyl mercaptan, so as to keep the cost of separating the methyl mercaptan produced as low as possible, for the process to be economically feasible. Here the cost of energy for cooling the reaction gas mixture to condense the methyl mercaptan is a major cost factor.

The aluminum oxide catalyst is usually activated with potassium tungstate to increase its activity and selectivity. The activator is usually used in proportions of up to 15% of the total weight of the catalyst. The activity and selectivity can also be improved by increasing the molar ratio of hydrogen sulfide to methanol. Usually molar ratios of 1 to 10 are used.

A high molar ratio, of course, means that the hydrogen sulfide is in great excess in the reaction gas mixture, so that large volumes of gas must be recirculated. The ratio of hydrogen sulfide to methanol should be only slightly different from 1 to reduce the cost of energy for recirculation. It is also desirable to carry out the reaction at the lowest possible temperature to reduce heat loss from the reactor.

U.S. Pat. No. 2,820,062 describes a process for producing organic thiols using an activated aluminum oxide catalyst which has been activated with potassium tungstate in proportions of 1.5% to 15% by weight, based on the weight of the catalyst. This catalyst gives good activities and selectivities at a reaction temperature of 400° C. and a molar ratio of 2. This U.S. patent mentions various possibilities for incorporating the potassium tungstate into the aluminum oxide, including impregnation processes, coprecipitations, and simple mixtures. The actual catalyst production is considered of little importance to the economics of the process for methyl mercaptan synthesis.

An object of this invention is to improve the methyl mercaptan synthesis in terms of improved activity and selectivity at low molar ratios of hydrogen sulfide to methanol, in comparison with the known methods using known catalysts, and which therefore gives a more economical process.

SUMMARY OF THE INVENTION

The above as well as other objects of the invention are achieved by a catalyst of aluminum oxide containing 5 to 25% by weight potassium tungstate as an activator on active aluminum oxide. This catalyst can be obtained by depositing the activator on the active aluminum oxide in two portions. The aluminum oxide is initially coated with the first portion of the promoter by impregnation with an excess of aqueous impregnating solution. Then it is dried at an elevated temperature before the second portion is applied to the aluminum oxide by pore volume impregnation. The catalyst precursor obtained in this way is dried again at elevated temperature and finally calcined at temperatures between 200° C. and 600° C.

The mass ratio of the two portions of the activator is preferably established so that the first portion of activator amounts to one third to two thirds of the total amount of activator. Tungstates of the alkali elements Li, Na, K and Rb or mixtures thereof can be used as promoters, though preferably only potassium is used.

BRIEF DESCRIPTION OF THE DRAWINGS

The invention will be further understood with reference to the drawings, wherein.

DETAILED DESCRIPTION OF THE INVENTION

Figure 1:
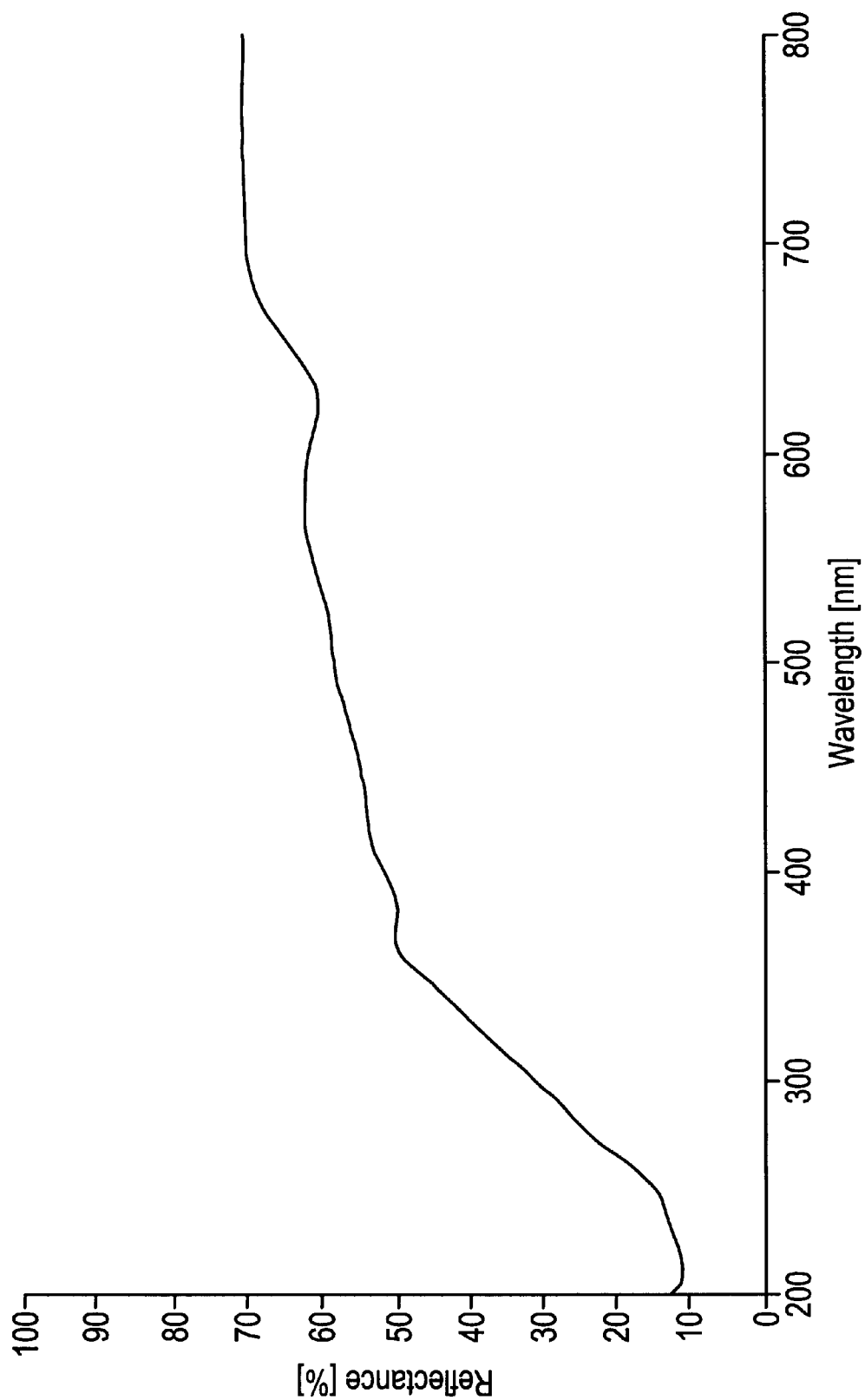
FIG. 1 is a graph of the reflectance spectrum of the catalyst of Comparison Example 1 measured versus a barium sulfate white standard.

In carrying out the present invention, so-called "active aluminum oxide" is used as the aluminum oxide for this catalyst. This material has high specific surface area from about 10 to 400 $m^2/g$, and consists primarily of oxides from the transitional series of the crystallographic phases of aluminum oxide (see, for instance, Ullmann's Encyclopedia of Industrial Chemistry, 1985, Vol. A1, pages 561–562). These transitional oxide phases include $\chi$, $\kappa$, $\gamma$, $\delta$, $\eta$, and $\theta$ aluminum oxide. All of these crystallographic phases convert to the thermally stable $\alpha$-aluminum oxide when the aluminum oxide is heated to temperatures above 1100° C. Active aluminum oxide is sold commercially in various qualities and physical forms for catalytic applications. Granulated or extruded aluminum oxide with particle diameters of 1 to 5 mm, specific surface areas of 180–400 $m^2/g$, total pore volumes of 0.3 to 1.0 ml/g, and bulk densities of 300–900 g/liter are quite well suited for the purposes of the present invention. The term "active aluminum oxides" is well known in the art and its art recognized meaning is used herein.

The activator, potassium tungstate, is deposited on the aluminum oxide in a two-step impregnation. In the first step, the aluminum oxide is impregnated with an excess of an aqueous impregnating solution of the activator or activators. In the second step, it is coated with the remaining amount of activator by pore volume impregnation. This special two-step impregnation with intermediate drying gives increased activity and selectivity of the finished catalyst in comparison with the single-step impregnation known in the state of the art, especially at low molar ratios of hydrogen sulfide to methanol.

The nature of the two impregnating steps is critically important for the activity and selectivity of the finished catalyst.

An aqueous solution of the activator is prepared for the first impregnating step. If the desired concentration and/or the limited solubility of the activator compound require, the temperature of the impregnating solution can be increased up to 95° C. The impregnating solution, which can still be hot, is poured over the aluminum oxide catalyst particles in a vessel until all particles are covered with the solution. The excess water is poured off after deposition of the activator compound, after about 20 to 60 minutes.

After the water is poured off, the catalyst particles are dried for 1 to 10 hours at an elevated temperature from 50° C. to 250° C., preferably from 100° C. to 140° C. That can be followed by calcination at temperatures from 400° C. to 600° C., particularly from 420° C. to 480° C., for a period of 1 to 5 hours. The drying can be preceded by preliminary drying at room temperature for up to 20 hours, preferably 10 to 14 hours. That improves the evenness of the impregnation across the cross section of the catalyst particles.

In the second impregnation step the remainder of the activator is added to the catalyst carrier by pore volume impregnation (also known as "incipient wetness impregnation"). In that process the remainder of the activator is dissolved in a volume of water which corresponds approximately to the water uptake capacity of the catalyst particles. Here, again, the solution can be heated to 95° C. to improve the solubility. This solution is slowly distributed over the catalyst carrier while it is being rotated in a coating pan. Then the catalyst carrier is dried as was done after the initial impregnation, and then calcined at temperatures in the range of 400° C. to 600° C. for 1 to 5 hours.

It is also desirable to precalcine the catalyst particles for 1 to 10 hours at temperatures in the range of 400° C. to 600° C. to attain optimal activity.

The amounts of activator applied in the two impregnating steps are preferably selected to be equally large. However, the proportion of activator applied in the first impregnating step can vary between one third and two thirds of the total amount of activator.

The procedure described for the impregnating steps is critically important for development of high activity and selectivity in the finished catalyst. Comparison experiments with single-step impregnations in excess and with one-stage and two-stage pore volume impregnations gave catalysts with lower activity and selectivity.

Before use in methyl mercaptan synthesis, the catalysts are pre-sulfided under conditions similar to those of the reaction ((V. Yu. Mashkin, Appl. Catal. A 109 (1994), pp. 45–61). That is done by passing a stream of hydrogen sulfide over the catalyst particles for 2 hours at 350° C. and a pressure of 9 bar. While catalysts according to the invention, and conventional catalysts, have a gray color on the outside and a white core before this treatment, distinct color differences are observed after the sulfiding. Conventionally produced catalysts show only slight color changes after sulfiding, while the catalysts produced according to the invention exhibit distinct yellow coloration after the sulfiding. That is considered due to increased production of thiotungstates. This coloration is not just superficial. Rather, it completely penetrates the catalyst particle.

Figure 2:
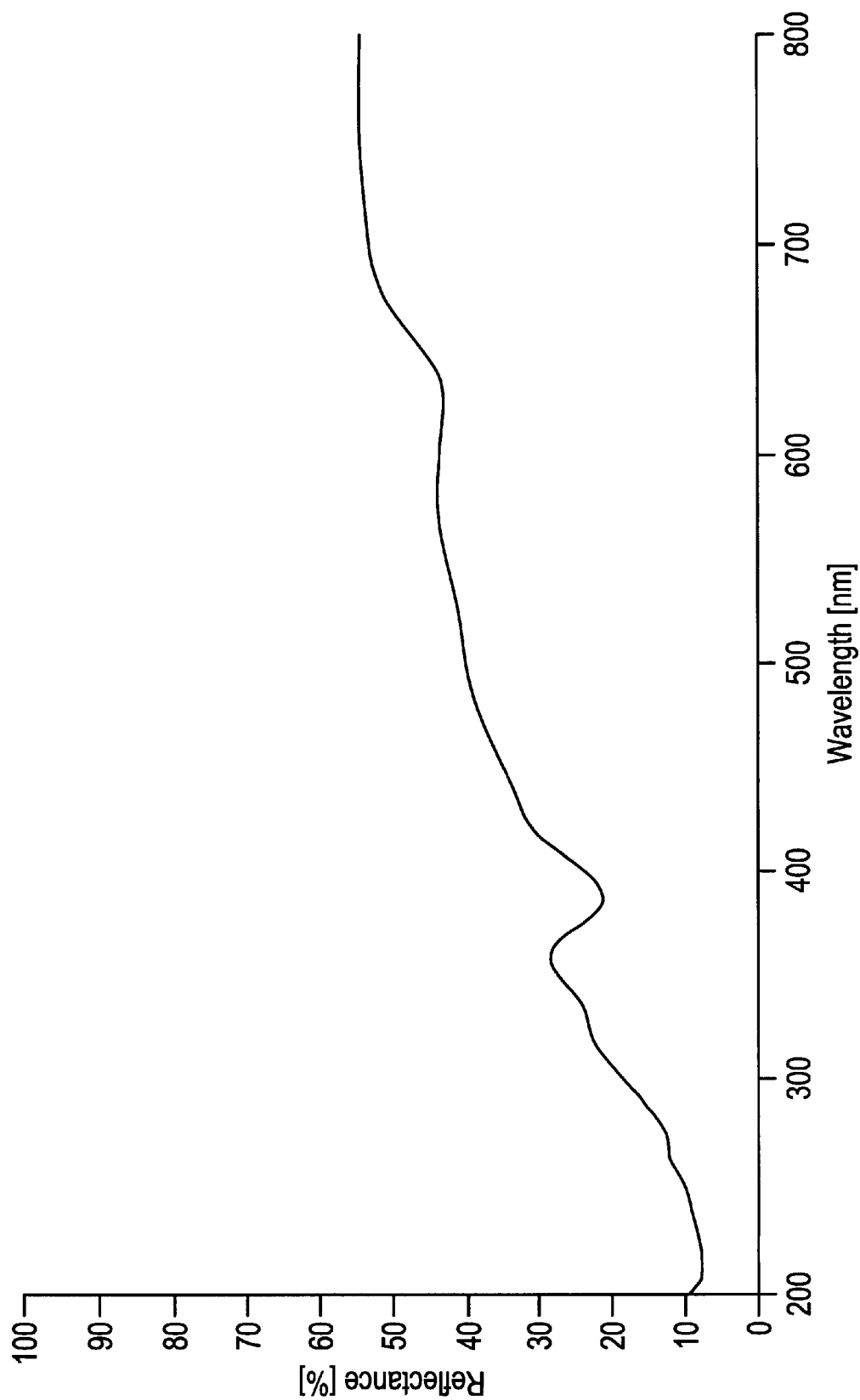
FIG. 2 is a graph of the reflectance spectrum of the catalyst of Example 1 measured versus a barium sulfate white standard.
Figure 3:
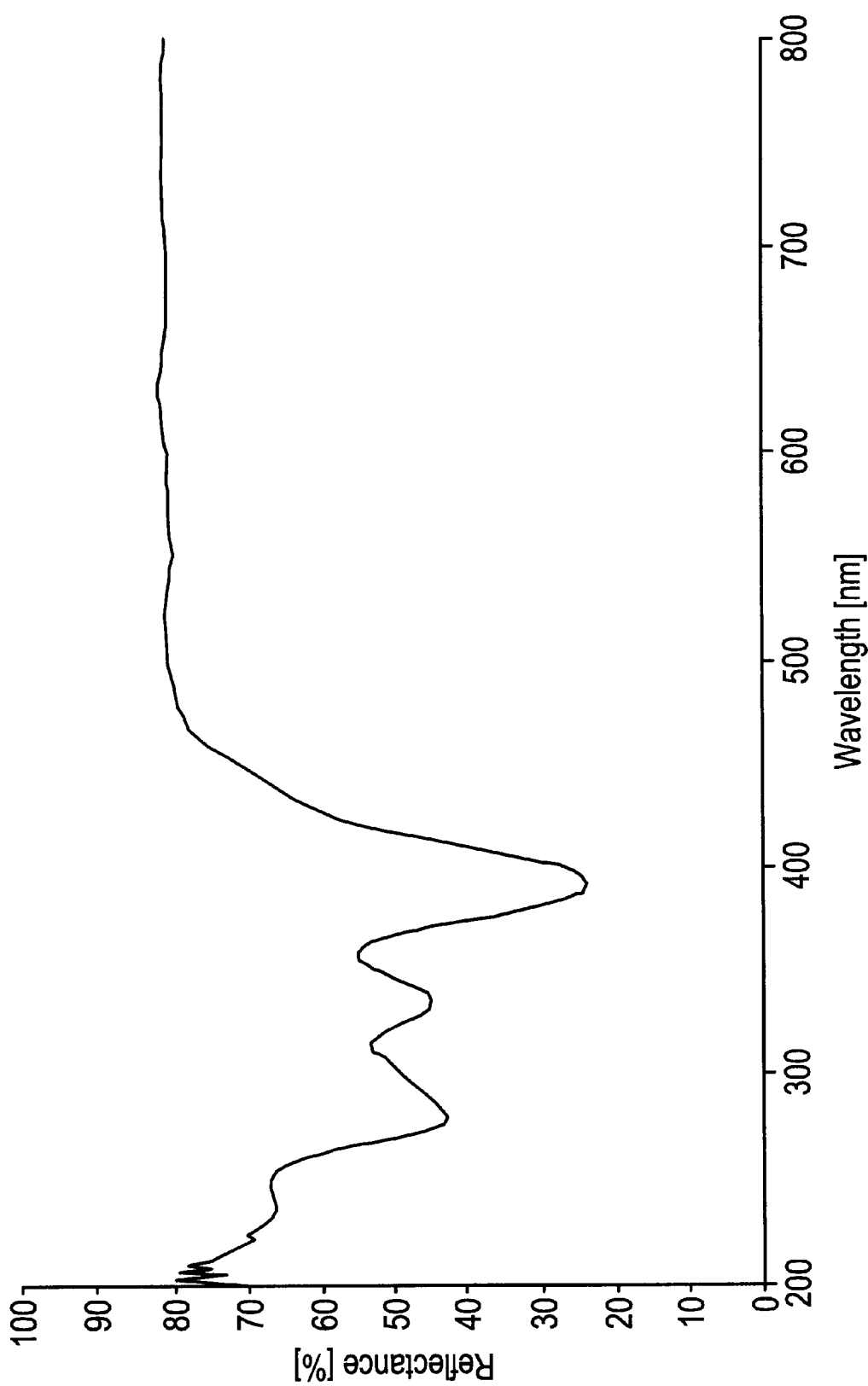
FIG. 3 is a graph of the reflectance spectrum of the catalyst of Example 1 measured versus the catalyst of Comparison Example 1.

The yellow coloration observed also appears in the reflectance spectrum of catalyst particles ground to powder by distinct absorption bands between 270 and 420 nm, compared with conventional catalysts. One absorption band in the wavelength range between 375 and 420 nm is particularly distinct. Somewhat weaker absorption bands appear in the wavelength regions between 270 and 290 nm and between 325 and 345 nm. FIGS. 1 to 3 show the reflectance spectra of catalysts according to the invention and comparison catalysts.

EXAMPLE 1

1.8 kg of granular aluminum oxide (Spheralite 501 A from Rhone-Poulenc; specific surface area 320 $m^2/g$; total pore volume 0.45 ml/g; bulk density 0.8 $g/cm^3$) was calcined for 4 hours in air at 455° C. A previously prepared solution of 8.7% by weight potassium tungstate in water at a temperature of 95° C. was poured over the granulation in a vessel until all the catalyst particles were covered. The excess water was poured off after a waiting period of 40 minutes. The moist catalyst particles were pre-dried in air at room temperature for 16 hours and then for 2 hours at 120° C. This treatment deposited 7% by weight potassium tungstate, i. e., 126 g, on the catalyst particles.

To carry out the pore volume impregnation, 162 g potassium tungstate was dissolved in 900 ml water, equivalent to 100% of the measured total pore volume of the catalyst material, at a temperature of 95° C. and distributed over the catalyst carrier in a rotating coating pan. That was followed by another 16-hour pre-drying in air and 2 hours of drying at 110° C. Finally the catalyst particles were calcined in air for 4 hours at 455° C.

The finished catalyst thus contained 288 g potassium tungstate on 1.8 kg aluminum oxide, amounting to 16% by weight potassium tungstate, based on the weight of the catalyst used.

EXAMPLE 2

A catalyst according to the invention was prepared as in Example 1 with 16% by weight potassium tungstate. This example differs from Example 1 in that the catalyst material was not calcined before application of the activator.

Comparison Example 1

A catalyst with 16% by weight potassium tungstate was prepared as in the preceding Example 1, starting with 1.5 kg aluminum oxide.

A hot solution (95° C.) of 17.4% by weight potassium tungstate in water was prepared and poured onto the catalyst particles until they were completely covered with solution. After 40 minutes the excess water was poured off and the catalyst material was predried, dried and calcined as in Example 1. The finished catalyst contained 16% by weight potassium tungstate, based on the weight of the aluminum oxide.

The catalyst pieces obtained in Example 1 and Comparison Example 1 had distinctly different colors after the pre-sulfiding. While the catalysts prepared according to the invention had a yellowish color, the comparison catalysts were white to grey. To measure the reflectance of the two materials, a certain amount of each catalyst was powdered and pressed into tablets. Their reflectances were measured in a Perkin-Elmer spectrometer versus a barium sulfate calibration standard. FIGS. 1 and 2 show the spectra measured. The catalyst according to the invention has a distinct absorption band below 420 nm which causes the yellow coloration observed. FIG. 3 shows the difference spectrum of the two reflectance spectra of FIGS. 1 and 2. The difference spectrum makes the differences between the two catalysts particularly clear. Three absorption bands appear here in the region between 270 and 420 nm.

Comparison Example 2

The procedure was the same as for Comparison Example 1, except that the entire amount of potassium tungstate was applied to the catalyst particles in one step by pore volume impregnation. In this process, 240 g potassium tungstate (16% by weight of the 1.5 kg of aluminum oxide used) was dissolved in 750 ml of water heated to 95° C. and distributed over the catalyst particles in a rotating coating pan.

Comparison Example 3

The procedure was the same as for Comparison Example 2, but the pore volume impregnation was done in two stages with intermediate drying of the catalyst particles. 120 g potassium tungstate was dissolved in 750 cm$^3$ for each impregnation stage.

The catalyst pieces obtained in the preceding examples were pre-sulfided before they were used to produce methyl mercaptan. Here it appeared that the catalysts prepared according to the invention had distinctly different colors from the comparison catalysts. While the catalysts prepared according to the invention had a yellowish color, the comparison catalysts were white to grey.

Application Example

The catalysts were tested for their capabilities in the synthesis of methyl mercaptan from hydrogen sulfide and methanol.

The synthesis was done in a stainless steel tube 500 mm long with an inside diameter of 14 mm. The catalyst packing, 32.4 ml in each case, was fixed in the reaction tube at both ends by inert packings of glass beads. The reaction tube was heated electrically to the reaction temperature of about 350° C.

The product, methyl mercaptan, with dimethyl sulfide, dimethyl ether, and unreacted methanol were washed out of the gas stream after cooling the product with methanol at 25° C. and worked up by distillation.

The following list shows the test conditions.

| | | |
|---|---|---|
| GHSV | 1280 hour$^{-1}$ | (based on standard conditions) |
| LHSV | 0.56 hour$^{-1}$ | (based on liquid MeOH) |
| Reaction temperature: | 357° C. | |
| Molar ratio: H$_2$S/MeOH: | 1.5 | |
| Pressure: | 9 bar | |

The following table shows the results of measurements by on-line gas chromatography of the reaction gas mixture. As can be seen from this table, the catalyst according to the invention of Example 1 gives higher selectivity at the same methanol conversion with the methyl mercaptan yield of about 2%, compared with the comparison catalyst of Comparison Example 2. When the synthesis of methyl mercaptan is done at large scale, this leads to substantial savings of cost in the separation of the reaction products. These results were obtained at a relatively low molar ratio of hydrogen sulfide to methanol of only 1.5 and at the reaction temperature of 357° C., which is relatively low in comparison with the state of the technology.

TABLE

Test results

| Catalyst | Methanol conversion (%) | Selectivity (%) |
|---|---|---|
| Example 1 | 90 | 91.3 |
| Example 2 | 87.9 | 91.2 |
| Comparison Example 1 | 89.9 | 88.7 |
| Comparison Example 2 | 90 | 89.2 |
| Comparison Example 3 | 89.5 | 89.0 |

The preceding discussions were limited for simplicity to the problems in the synthesis of methyl mercaptan. It will be clear to one skilled in the art, though, that the catalyst according to the invention is also suitable for synthesis of mercaptans generally by catalytic reaction of olefinic hydrocarbons with hydrogen sulfide.

Further variations and modifications of the foregoing will be apparent to those skilled in the art and are intended to be encompassed by the claims appended hereto.

German priority application 196 39 520.8 is relied on and incorporated herein by reference.

We claim:

1. A precursor for a catalyst for alkyl mercaptan synthesis exhibiting improved activity and selectivity at low molar ratios of hydrogen sulfide to alkanol, produced by a process comprising:

depositing potassium tungstate as an activator on active aluminum oxide in two separate portions, by:
depositing on the aluminum oxide a first portion of the activator by impregnation in an excess of an aqueous impregnating solution for about 20–60 minutes;
drying a first time for 1 to 10 hours at a temperature from 50° C. to 250° C.;
depositing a second portion on the aluminum oxide by pore volume impregnation;
drying a second time for 1 to 10 hours at a temperature from 50° C. to 250° C.; and then,
calcining at a temperature from 400° C. to 600° C. for 1 to 5 hours,
the resulting catalyst precursor comprising active aluminum oxide containing from 5 to 25% by weight potassium tungstate as an activator.

2. The catalyst precursor according to claim 1, wherein the first portion of the activator deposited is from about one third to about two thirds of the total amount of the activator.

3. The catalyst precursor according to claim 1, wherein the active aluminum oxide is calcined for 1 to 10 hours at temperatures from 400° C. to 600° C. before deposition of the activator.

4. The catalyst precursor according to claim 1, wherein the catalyst precursor produced exhibits a reflectance spectrum corresponding to FIG. 2 after being contacted with a stream of hydrogen sulfide for two hours at a temperature of 350° C. and a pressure of 9 bar, and then ground to a powder and pressed into tablets.

5. The catalyst precursor according to claim 1, further characterized in that, when the catalyst precursor is contacted with a stream of hydrogen sulfide for two hours at 350° C. and a pressure of 9 bar, the color of the catalyst precursor changes from a gray color to a yellow color.

6. The catalyst precursor according to claim 1, wherein after the aluminum oxide is first dried, and before the second portion of the activator is deposited, the aluminum oxide is calcined at a temperature from 400° C. to 600° C. for a period from 1 to 5 hours.

7. The catalyst precursor according to claim 1, wherein the pore volume impregnation deposition step comprises:
   dissolving the second portion of the activator in a volume of water which corresponds approximately to a water uptake capacity of the aluminum oxide; and
   distributing the volume of water over the aluminum oxide while rotating the aluminum oxide in a coating pan.

8. The catalyst precursor according to claim 1, wherein the drying the first time at elevated temperature is preceded by a preliminary drying at room temperature for 10 to 14 hours.

9. A method of alkyl mercaptan synthesis, comprising:
   contacting the catalyst precursor according to claim 1 with a stream of hydrogen sulfide for two hours at 350° C. and a pressure of 9 bar to create a catalyst for alkyl mercaptan synthesis; and,
   reacting an alkanol with hydrogen sulfide in the presence of the catalyst.

10. The method of alkyl mercaptan synthesis according to claim 9, wherein the alkanol is methanol.

11. A catalyst for alkyl mercaptan synthesis having improved activity and selectivity at low molar ratios of hydrogen sulfide to alkanol, produced by a process comprising:
    depositing the activator on the active aluminum oxide in two separate portions, by:
      depositing on the aluminum oxide a first portion of the activator by impregnation in an excess of an aqueous impregnating solution for about 20–60 minutes;
      drying a first time for 1 to 10 hours at a temperature from 50° C. to 250° C.; and
      depositing a second portion on the aluminum oxide by pore volume impregnation;
      drying a second time for 1 to 10 hours at a temperature from 50° C. to 250° C.;
    calcining at a temperature from 400° C. to 600° C. for 1 to 5 hours, the resulting product comprising active aluminum oxide containing from 5 to 25% by weight potassium tungstate as an activator; and
    pre-sulfiding by contacting with a stream of hydrogen sulfide for two hours at 350° C. and a pressure of 9 bar, during which the color changes from a gray color to a yellow color.

12. The catalyst according to claim 11, wherein the first portion of the activator deposited is from about one third to about two thirds of the total amount of the activator.

13. The catalyst according to claim 11, wherein the active aluminum oxide is calcined for 1 to 10 hours at temperatures from 400° C. to 600° C. before deposition of the activator.

14. The catalyst according to claim 11, wherein the catalyst produced exhibits a reflectance spectrum corresponding to FIG. 2 after being ground to a powder and pressed into tablets.

15. The catalyst according to claim 11, wherein the two activator deposition steps are at a temperature of about 95° C.

16. The catalyst according to claim 11, wherein after the aluminum oxide is first dried, and before the second portion of the activator is deposited, the aluminum oxide is calcined at a temperature from 400° C. to 600° C. for a period from 1 to 5 hours.

17. The catalyst according to claim 11, wherein the pore volume impregnation deposition step comprises:
    dissolving the second portion of the activator in a volume of water which corresponds approximately to a water uptake capacity of the aluminum oxide; and
    distributing the volume of water over the aluminum oxide while rotating the aluminum oxide in a coating pan.

18. The catalyst according to claim 11, wherein the drying the first time at elevated temperature is preceded by a preliminary drying at room temperature for 10 to 14 hours.

19. A precursor for a yellow catalyst for alkyl mercaptan synthesis exhibiting improved activity and selectivity at low molar ratios of hydrogen sulfide to alkanol, produced by a process comprising:
    depositing potassium tungstate as an activator on active aluminum oxide in two separate portions, by:
      depositing on the aluminum oxide a first portion of the activator by impregnation in an excess of an aqueous impregnating solution for about 20–60 minutes;
      drying a first time for 1 to 10 hours at a temperature from 50° C. to 250° C.;
      depositing a second portion on the aluminum oxide by pore volume impregnation;
      drying a second time for 1 to 10 hours at a temperature from 50° C. to 250° C.; and then,
    calcining at a temperature from 400° C. to 600° C. for 1 to 5 hours,
    the resulting catalyst precursor comprising active aluminum oxide containing from 5 to 25% by weight potassium tungstate as an activator.

20. A yellow catalyst for alkyl mercaptan synthesis having improved activity and selectivity at low molar ratios of hydrogen sulfide to alkanol, produced by a process comprising:
    depositing the activator on the active aluminum oxide in two separate portions, by:
      depositing on the aluminum oxide a first portion of the activator by impregnation in an excess of an aqueous impregnating solution for about 20–60 minutes;
      drying a first time for 1 to 10 hours at a temperature from 50° C. to 250° C.; and
      depositing a second portion on the aluminum oxide by pore volume impregnation;
      drying a second time for 1 to 10 hours at a temperature from 50° C. to 250° C.;
    calcining at a temperature from 400° C. to 600° C. for 1 to 5 hours, the resulting product comprising active aluminum oxide containing from 5 to 25% by weight potassium tungstate as an activator; and
    pre-sulfiding by contacting with a stream of hydrogen sulfide for two hours at 350° C. and a pressure of 9 bar, during which the color changes from a gray color to a yellow color.

* * * * *